United States Patent
Wessman et al.

(10) Patent No.: US 6,493,590 B1
(45) Date of Patent: Dec. 10, 2002

(54) FLEXIBLE BAND ELECTRODES FOR MEDICAL LEADS

(75) Inventors: Bradley J. Wessman, Maple Grove; Peter J. Pohndorf, Stillater; Paul J. Robinson, Mahtomedi, all of MN (US)

(73) Assignee: MicroNet Medical, Inc., White Bear Lake, MN (US)

( * ) Notice: Subject to any disclaimer, the term of this patent is extended or adjusted under 35 U.S.C. 154(b) by 0 days.

(21) Appl. No.: 09/500,611

(22) Filed: Feb. 9, 2000

(51) Int. Cl.⁷ ................................................. A61N 1/05
(52) U.S. Cl. ..................... 607/116; 607/119; 607/122
(58) Field of Search ........................ 607/116–119, 122

(56) References Cited

U.S. PATENT DOCUMENTS

| | | | |
|---|---|---|---|
| 4,308,868 A | 1/1982 | Jhabvala | 128/421 |
| 5,329,923 A * | 7/1994 | Lundquist | 607/122 |
| 5,411,546 A | 5/1995 | Bowald et al. | 607/126 |
| 5,487,757 A | 1/1996 | Truckai et al. | 607/122 |
| 5,558,073 A | 9/1996 | Pomeranz et al. | 128/642 |
| 5,562,722 A | 10/1996 | Racz et al. | 607/117 |
| 5,582,609 A | 12/1996 | Swanson et al. | 606/39 |
| 5,645,580 A | 7/1997 | Moaddeb et al. | 607/122 |
| 5,676,662 A | 10/1997 | Fleischhacker et al. | 606/41 |
| 5,728,149 A * | 3/1998 | Laske et al. | 607/122 |
| 5,833,632 A * | 11/1998 | Jacobsen et al. | 600/585 |
| 5,876,443 A | 3/1999 | Hochmair et al. | 623/10 |
| 6,246,914 B1 * | 6/2001 | de la Rama et al. | 607/122 |

* cited by examiner

*Primary Examiner*—Carl Layno
(74) *Attorney, Agent, or Firm*—Kevin W. Cyr; Briggs and Morgan, P.A.

(57) ABSTRACT

An apparatus is provided for use in stimulating a body tissue or organ that has a flexible band electrode. The band electrode includes at least one slot configured to provide increased flexibility. A lead having the electrode is also provided as well as a method for manufacturing a band electrode having at least one slot.

11 Claims, 1 Drawing Sheet

FLEXIBLE BAND ELECTRODES FOR MEDICAL LEADS

BACKGROUND OF THE INVENTION

1. Field of the Invention

This invention relates generally to catheters and leads used in sensing electrical activity within a patient and administering therapy, and more particularly to such catheters and leads incorporating band electrodes configured for improved flexibility and tractability within the body.

2. Discussion of the Related Art

A variety of medical electrode catheters are available today for the diagnosis and treatment of various disorders of the cardiovascular and neurological systems. These electrode catheters can be used to sense electrical activity within the body and to deliver different forms of energy to stimulate, ablate, cauterize or pace. The core electrode technology common to all of these catheter designs is the application of one or more metallic bands on a catheter body. Examples of medical catheters using metallic banded electrodes include permanent and temporary cardiac pacing leads, electro-physiologic (EP) catheters, electrocautery probes and spinal stimulation catheters. The use of preformed metallic band electrodes manufactured from noble metals, such as gold or platinum and various other conductive alloys has found widespread application despite their functional design and performance limitations.

Metallic band electrodes possess distinct steerability problems. The steerability problems arise from the inflexible nature of the circular rings or bands. These inflexible bands of metal are typically adhesively bonded, crimped or otherwise attached to the exterior surface of the catheter or lead body. The bands are electrically coupled to electrical conductors that typically extend through one or more lumens in the catheter or lead body. The bands tend to be relatively thick and are therefore rigid. For neurological applications, the bands are typically about 3 millimeters wide. When it is considered that four or eight such ring electrodes are typically spaced about four millimeters apart along the distal end portion of the catheter body, they significantly impact the ability of the distal end portion of the catheter or lead to flex and conform to tissue structures.

As noted above, band electrodes placed on a flexible catheter or lead stiffen the catheter or lead and thereby reduce steerability. As such, catheters and leads having band electrodes are often restricted to applications where steerability and selective placement are not required. The steerability and placement problems of leads and catheters affect a variety of applications.

In cardiac therapies, such as for example ablation therapy, precise steerability and placement of a catheter is necessary. Ablation therapy requires that a catheter having sensing/ablation electrodes on the distal end is steered through the patient's vascular system and into a predetermined chamber of the heart. The catheter is manipulated so as to place the electrodes into direct contact with the myocardial tissue that is sensed and/or to be ablated. The aberrant path and/or ectopic foci is first located using a mapping technique in which cardiac depolarization signals picked up by the electrodes are transmitted over electrical conductors in the lead to a suitable monitor/analyzer. Once located, the aberrant conductive pathway or the ectopic foci is ablated. This procedure requires the ability to precisely control the catheter over the surfaces of the heart. Therefore, a need exists for a catheter that provides precise control and steerability to accurately locate the electrodes in the heart.

In neurological therapies, such as for example neuromodulation, precise steerability and placement of a catheter is also necessary. Neuromodulation typically requires multi-electrode catheters be surgically implanted adjacent the spinal chord to stimulate the regions of the spinal cord that correspond to the regions of the body being treated. However, spinal cord stimulation has limited effectiveness for certain pain conditions. In many cases where spinal cord stimulation is inadequate, spinal nerves or peripheral nerves must be stimulated to provide relief from pain and other neurological conditions. However, with existing technology, spinal nerve or peripheral nerve stimulation cannot be accomplished without a surgical implant because appropriately sized leads having sufficiently steerability are unavailable. Surgical implants result in scarring and significant discomfort to the patient. Therefore, a need exists for a lead having enhanced steerability that provides greater specificity and increased accessibility to perform a broader array of nerve stimulation, while using less invasive methods to improve treatment outcome.

In addition, clinical studies have shown that spinal cord stimulation requires substantially more power to negate pain than direct stimulation of spinal or other peripheral nerve stimulation. For example, spinal cord stimulation typically requires the delivery of about 2 to 4 volts to effectively suppress pain whereas only about half or 1 to 2 volts need be delivered to spinal nerves or peripheral nerves to achieve the similar pain suppression. Higher energy requirements reduce battery life and, in turn, increase the frequency of surgery to replace the implanted battery-powered pulse generators. Therefore, a need exists for a neurostimulating lead that can be advanced to a location adjacent selected spinal nerve or peripheral nerve to reduce the energy requirements of neuromodulation.

The present invention meets the above needs and additional needs that will be recognized by those skilled in the art. The present invention provides a band electrode having increased flexibility. The present invention provides a method for manufacturing a lead having a high degree of steerability. The present invention provides a novel method for manufacturing a flexible band electrode and an electrical lead having a reduced diameter and at least one flexible electrode at or near the lead's distal end. A lead manufactured in accordance with the present invention enables a novel neuromodulation method in which stimulating leads are percutaneously placed in the epidural space and advanced over a guidewire or using a stylet through a selected intervertebral foramen. In addition, upon review of the disclosure, those skilled in the art will recognize additional advantages and improvements conferred by the present invention.

SUMMARY OF THE INVENTION

The present invention provides a band electrode and a lead having a band electrode for a medical device and a method for manufacturing a band electrode. The band electrode including a conductive band having at least one slot cut through the conductive band to confer flexibility. The band electrode may be comprised of a conductive band having an outside diameter between about 2 French and about 12 French. The conductive band may be a material selected the group of platinum, gold, silver, platinum-iridium, stainless steel and MP35N or may be an alloy thereof. The lead for a medical device includes the band electrode as describe above and further includes a lead body having a conductor extending from a proximal end and a distal end of the lead body connected at one end to the band electrode. The lead body may have an outside diameter between about 2 French and about 12 French. The electrode and lead may be made by a method comprising providing a conductive cylindrical band and cutting at least one slot through the band to confer flexibility.

DETAILED DESCRIPTION OF THE INVENTION

Figure 1:
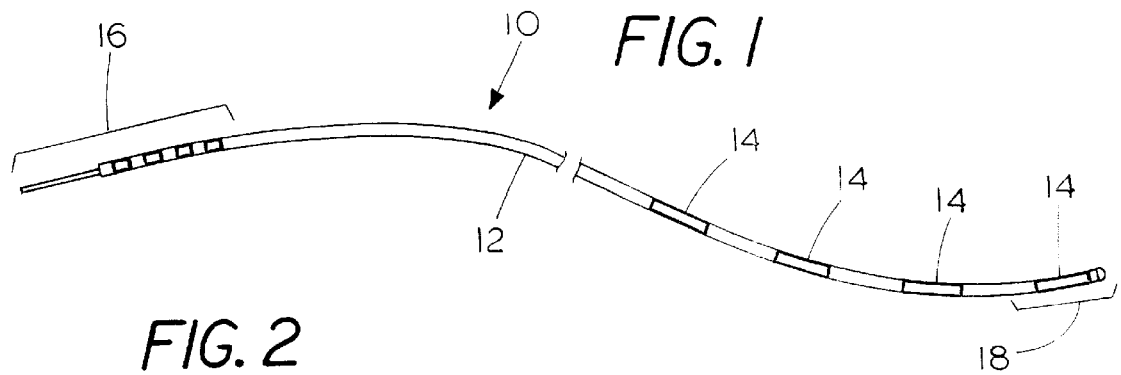
FIG. 1 illustrates a partial perspective view of a lead constructed in accordance with the present invention.

The present invention is provides a flexible band electrode for placement on an implantable lead or catheter. The invention is described in the context of an electrode for a neurostimulating lead and a method for manufacturing a neurostimulating electrode as a specific example for illustrative purposes only. The appended claims are not intended to be limited to any specific example or embodiment described in this patent. It will be understood by those skilled in the art that the electrode of the present invention may be used for a wide variety of leads and catheters including, but not limited to, leads and catheters for use with cardiac monitoring devices, cardiac rhythm management devices, ablation devices, mapping devices, neurostimulating devices, neuromonitoring devices or other medical devices using leads or catheters. Further, in the drawings described below, the reference numerals are generally repeated where identical elements appear in more than one figure.

FIG. 1 illustrates an embodiment of a lead 10 made in accordance with the present invention. Leads designed for neurostimulation typically have four or more longitudinally spaced ring electrodes at the lead's distal end. Lead 10, as shown, includes a lead body 12, a series of four band electrodes, each numbered as 14, and a connective region 16. Lead 10 is generally configured to transmit an electric signal from a pulse generator (not shown) to a spinal nerve or peripheral nerve. Lead 10 is further configured to permit insertion through the epidural space and guiding of band electrode to a target location along a selected spinal nerve or peripheral nerve. Alternatively, lead 10 may be configured to permit insertion through the skull to a location for deep brain stimulation. In yet another alternative, lead 10 may be configured to facilitate placement adjacent to a peripheral nerve through a route other than the spinal column. Lead body 12 includes a flexible lead insulator surrounding one or more conductors. Lead body 12 includes a proximal end and a distal end. Connective region 16 is provided at the proximal end of lead body 12. Connective region 16 is generally configured to form an electrical connection with the pulse generator either with or without an adaptive fitting. Connective region 16 may be isodiametric with lead body 12, as shown in FIG. 1, wherein the region will typically require an adaptive fitting, not shown, or alternatively, may take the form of a connector pin configured to electrically couple the lead to a pulse generator without an adaptive fitting.

Typically, lead body 12 is a flexible, elastomeric structure having a round cross-section. Alternatively, lead body's cross-section could be any number of shapes appropriate for the specific application. The lead insulator is generally configured to insulate the conductors and to present a smooth biocompatible external surface to body tissues. Thus, the lead insulator is typically coextensive with conductors. The material of lead insulator is typically selected based on biocompatibility, biostability and durability for the particular application. The lead insulator may be silicone, polyurethane, polyethylene, polyimide, polyvinylchloride, PTFE, ETFE, or other materials known to those skilled in the art. Moreover, alloys of these materials as well as blends thereof may also be formulated in known manners to control the relative flexibility, torqueability, and pushability of the lead. Those skilled in the art will also recognize that the material of the lead body may be designed to have an inherent memory property whereby the distal end portion will assume a predetermined shape configuration when in a free state, i.e., without any external forces acting on the lead body. The lead body is typically steerable in that the body may include steering elements (not shown) that enable the distal end to be deformed to allow the lead to steer through a lumen, a tissue, or a matrix. Typically, the steering elements include steering wires running through the body attached to the distal end and extending through the proximal end that enable the user to steer the lead into position. Alternatively, the flexibility imparted by the flexible electrodes permits enhanced steerability when the lead is inserted over a guidewire or through catheter. Depending on the particular application, the diameter of the lead body may be as small as 2 French or smaller for neurological and myocardial mapping/ablation leads and can be sizes larger than 12 French for other applications.

The lead body includes at least one conductor. The conductors may be disposed within lumen within the lead body or the conductors may be integrally co-extruded into the material of the lead body. The conductors typically extend longitudinally from the distal end to the proximal end of the lead body. The conductors typically take the form of one or more stranded cables, wound wires, or ribbon wires. Thus, the conductors may be coaxial with the lead body or spirally, helically or otherwise wound within the lead body. The conductors may be composed of drawn-filled-tube (DFT), stainless steel, MP35N, drawn-brazed-strand (DBS) or other conductive materials known to those skilled in the art. The number, size, and composition of the conductors will depend on particular application for the lead. The conductors may be coupled to a connector pin or directly to the pulse generator at their proximal end or may be directly connected to a pulse generating or sensing device.

At least one band electrode 14 is positioned at the distal end of lead body 12 for electrically engaging a target tissue or organ. The band electrodes may be manufactured separately and then assembled onto the lead body or the electrodes may be integrally formed into the lead body. The band electrodes can be manufactured by extruding, molding, rolling or machining from the conductive material into the particular cross-sectional shaped band. At least one slot is typically cut into the band, unless the band is molded. If the band is molded, the slot is typically molded into the band for manufacturing efficiency. In the context of the claims, the term "cut" is intended to include molding a slot into the band electrode. The method for cutting the slots in smaller bands, such as those used for neurostimulation, typically uses a laser. Although, slots may be formed in a number of ways, including methods such as EDM, a mechanical blades or an abrasive wheel, that will be recognized by those skilled in the art. If the band is cut while on the lead body, the slot may extend into the material of the lead body. When the bands are rolled, the slots may be cut into the bands after the bands are formed or into the flat sheet before the bands are formed. When the slots are cut into the bands the method used for cutting depends on the size and composition of the band. When a plurality of electrodes 14 are used, the electrodes are typically spaced along the longitudinal axis of lead body 12. The band electrodes are electrically coupled to the conductors in a configuration appropriate for the particular application. The electrodes may be coupled to the conductors using electroplating, welding, crimping, conductive adhesive bonding, intertwining the conductor and the electrode or by other methods known to those skilled in the art. The electrodes are made of a conductive material such as platinum, gold, silver, platinum-iridium, stainless steel, MP35N or other conductive metals or alloys thereof known to those skilled in the art. As discussed above, the cross-sectional shape is typically round. Band electrodes 14 are typically shaped to conform to the outer surface of lead body 12. Therefore, typically if the lead body has a non-circular cross-section, for example, square, rectangular, triangular or oval, the band electrode will typically have a corresponding cross-section. Although, it is conceivable for some applications the band will have a cross-sectional shape that does not correspond to the lead body. For neurostimulation, band electrodes 14 are typically between 1 and 10 millimeters long and have a diameter between about 2 and about 8 French but are more typically between 4 and 6 French.

Figure 2:
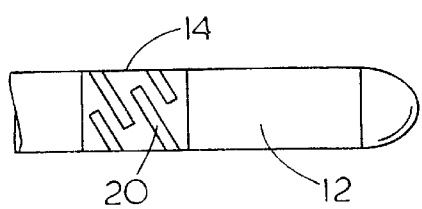
FIG. 2 illustrates an enlarged partial side view of an embodiment showing a band electrode having a plurality of cuts electrode.
Figure 3A:
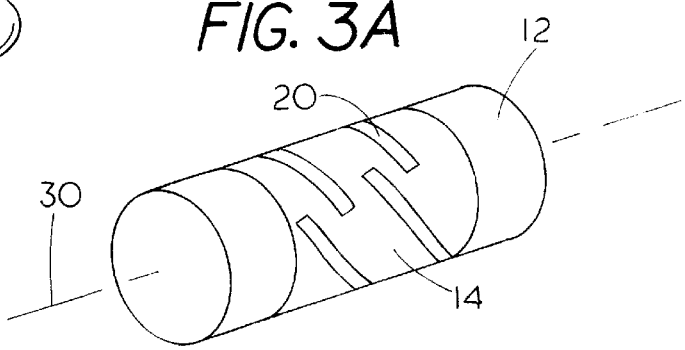
FIG. 3A illustrates a partial perspective view of an embodiment of the band electrode.
Figure 3B:
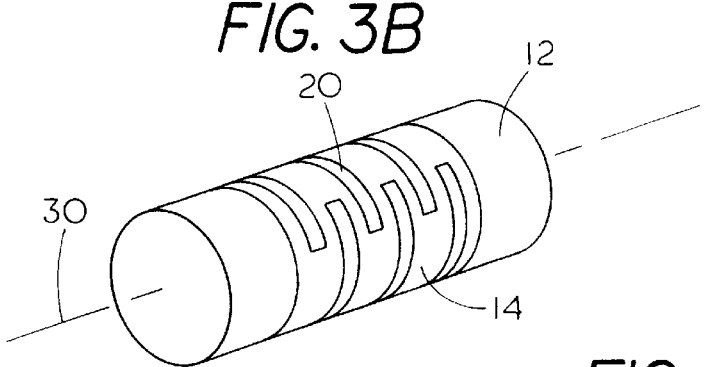
FIG. 3B illustrates a partial perspective view of an alternative embodiment of the band electrode.
Figure 3C:
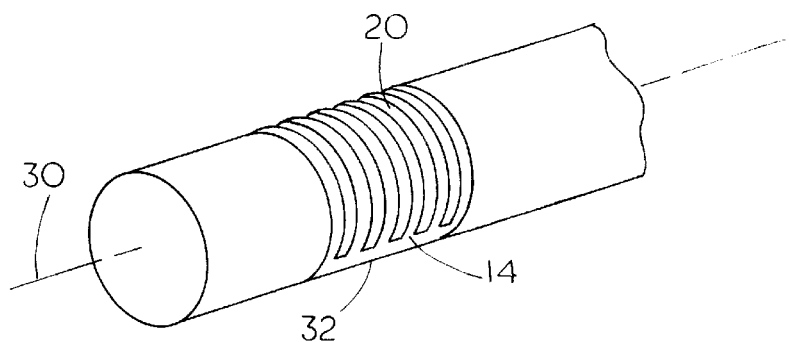
FIG. 3C illustrates a partial perspective view of yet another embodiment of the band electrode.

FIG. 2 illustrates the details of a band electrode 14 from region 18 of FIG. 1. The band electrodes of the present invention include at least one slot 20 or cut through the bands conductive material. Band electrode 14 of FIG. 2 includes a plurality of slots 20. The slots are configured to enhance the flexibility of the band electrodes. FIGS. 3A–C illustrate the details of an exemplary range of configurations to increase flexibility. FIGS. 3A–C are provided for illustrative purposes only and not intended to in any way limit the scope of the present invention. FIG. 3A shows a band electrode having slots 20 cut at an angle to the electrode's longitudinal axis 30. FIG. 3B shows a band electrode having slots 20 cut substantially perpendicular to the electrode's longitudinal axis 30. FIG. 3C. shows a band electrode 14 having a plurality of slots 20 cut into the band so as to facilitate the flexing of band 14 about an axis 32 established by the slot configuration. As exemplified and discussed above, it will be understood by those skilled in the art that a wide variety of slots configurations could be cut into the band electrodes to confer flexibility. The configurations generally include those that confer more flexibility and, particularly, those that confer more flexibility in certain directions than in others. The figures provide some examples of such configurations. The slots may preferentially confer flexibility on the electrode within a certain single plane, as best exemplified in FIG. 3B. Alternatively, the slots may confer flexibility about a particular axis, as best exemplified in FIG. 3C. Thus, the slots may be configured to preferably flex in certain directions, as may be appropriate for a particular application, or they may be configured to generally increase flexibility.

What is claimed is:

1. A band electrode for a medical device, comprising a conductive band configured to be secured to an exterior surface of a lead body with the conductive band having at least one slot cut through the conductive band to confer flexibility.

2. A band electrode, as in claim 1, wherein the conductive band has a plurality of slots cut through the conductive band with each of the plurality of slots extending through a line perpendicular to a longitudinal axis of the conductive band.

3. A band electrode, as in claim 1, wherein the conductive band has an outside diameter between about 2 French and about 12 French.

4. A band electrode, as in claim 1, wherein the conductive band has an outside diameter of between about 2 French and about 4 French.

5. A band electrode, as in claim 1, wherein the conductive band is a material selected the group consisting of platinum, gold, silver, platinum-iridium, stainless steel and MP35N.

6. A method for manufacturing a band electrode for attachment to an exterior surface of a lead body, comprising:
   providing a conductive cylindrical band; and
   cutting at least one slot through the conductive cylindrical band to confer flexibility to the conductive cylindrical band.

7. A lead for a medical device, comprising:
   a lead body having a conductor extending from a proximal end and a distal end of the lead body; and
   at least one band electrode configured as a cylindrical band having at least one slot cut into the band to confer flexibility, wherein the electrode is secured to an exterior surface of the lead body.

8. A lead, as in claim 7, wherein the band electrode has a plurality of slots cut through the conductive band.

9. A lead, as in claim 7, wherein the lead body has an outside diameter between about 2 French and about 12 French.

10. A lead, as in claim 7, wherein the lead body has an outside diameter of between about 2 French and about 4 French.

11. A lead, as in claim 7, wherein the band electrode is a material selected the group consisting of platinum, gold, silver, platinum-iridium, stainless steel and MP35N.

* * * * *